United States Patent
Gifford et al.

(10) Patent No.: US 9,971,976 B2
(45) Date of Patent: May 15, 2018

(54) ROBUST SELECTION OF CANDIDATES

(71) Applicant: International Business Machines Corporation, Armonk, NY (US)

(72) Inventors: Wesley M. Gifford, Ridgefield, CT (US); Pavankumar Murali, Elmsford, NY (US); Anshul Sheopuri, Teaneck, NJ (US)

(73) Assignee: International Business Machines Corporation, Armonk, NY (US)

( * ) Notice: Subject to any disclaimer, the term of this patent is extended or adjusted under 35 U.S.C. 154(b) by 831 days.

(21) Appl. No.: 14/493,504

(22) Filed: Sep. 23, 2014

(65) Prior Publication Data
US 2016/0085754 A1    Mar. 24, 2016

(51) Int. Cl.
*G06F 17/30* (2006.01)
*G06Q 10/00* (2012.01)
*G06F 19/00* (2018.01)

(52) U.S. Cl.
CPC ......... *G06Q 10/00* (2013.01); *G06F 17/3053* (2013.01); *G06F 17/30867* (2013.01); *G06F 19/3431* (2013.01)

(58) Field of Classification Search
None
See application file for complete search history.

(56) References Cited

U.S. PATENT DOCUMENTS

| | | | | |
|---|---|---|---|---|
| 5,560,005 A * | 9/1996 | Hoover | | G06F 17/30575 |
| 2002/0032600 A1 | 3/2002 | Royall, Jr. et al. | | |
| 2007/0218450 A1 * | 9/2007 | MacClay | | G09B 7/00 |
| | | | | 434/353 |
| 2009/0187473 A1 * | 7/2009 | Blaze | | G06Q 10/06 |
| | | | | 705/321 |
| 2010/0169106 A1 * | 7/2010 | Powers | | G06Q 10/1053 |
| | | | | 705/1.1 |
| 2011/0209119 A1 * | 8/2011 | Duesterwald | | G06F 8/72 |
| | | | | 717/122 |
| 2012/0221378 A1 * | 8/2012 | Thell | | G06Q 10/06398 |
| | | | | 705/7.32 |
| 2012/0330704 A1 | 12/2012 | Davidson | | |
| 2013/0080346 A1 | 3/2013 | Powell et al. | | |
| 2014/0095401 A1 * | 4/2014 | Merrill | | G06Q 10/1053 |
| | | | | 705/321 |

(Continued)

FOREIGN PATENT DOCUMENTS

WO     2003049004 A2     6/2003

OTHER PUBLICATIONS

Akoka et al., "A blackboard system for evaluating candidates to information systems positions.", Fifth International Conference on Expert Systems Applications "EXPERSYS-93", Paris, Dec. 6-7, 1993, pp. 245-250.

(Continued)

*Primary Examiner* — Son T Hoang
(74) *Attorney, Agent, or Firm* — Andrew Aubert

(57) ABSTRACT

Selecting candidates from a set of candidates by receiving a set of input parameters about a single aspect of the candidates and applying multiple scoring methods to those input parameters to compute a candidate score via each scoring method. A subset of zero or more candidates is then selected from the set of candidates by applying one or more selection criteria to the set of scores. There is not necessarily a value for every input parameter of every candidate.

20 Claims, 7 Drawing Sheets

(56) References Cited

U.S. PATENT DOCUMENTS

2014/0141401 A1* 5/2014 Agarwal ............... G09B 19/00
434/359

OTHER PUBLICATIONS

Albanese et al., "Assessing Personal Qualities in Medical School Admissions", Academic Medicine, vol. 78, No. 3, Mar. 2003, pp. 313-321.

Epple et al., "Peer Effects, Financial Aid, and Selection of Students into Colleges and Universities: An Empirical Analysis", Mar. 16, 2001, pp. 1-52.

Espenshade et al., "Admission Preferences for Minority Students, Athletes, and Legacies at Elite Universities", Social Science Quarterly, vol. 85, No. 5, Dec. 2004, pp. 1422-1446.

Ibm et al., "The method to identify candidates to be re-considered for adoption used in the tool to support investment valuation", an IP.com Prior Art Database Technical Disclosure, Original Publication Date: Aug. 27, 2004, IP.com No. IPCOM000030799D, IP.com Electronic Publication: Aug. 27, 2004, pp. 1-4.

Ellen R. Julian, PhD, "Validity of the Medical College Admission Test for Predicting Medical School Performance", Research Report, Academic Medicine, vol. 80, No. 10 / Oct. 2005, pp. 910-917.

Lievens et al., "The Validity of Interpersonal Skills Assessment Via Situational Judgment Tests for Predicting Academic Success and Job Performance", Research Report, Journal of Applied Psychology 2012, vol. 97, No. 2, 460-468, © 2011 American Psychological Association, DOI: 10.1037/a0025741, pp. 460-468.

William E. Sedlacek, "Using Noncognitive Variables in Assessing Readiness for Higher Education", (in press) Diversity, Merit, and Higher Education: Toward a Comprehensive Agenda for the 21st Century. AMS Press. Brooklyn, NY, 2005.

Sternberg et al., "Does the Graduate Record Examination Predict Meaningful Success in the Graduate Training of Psychologists?" A Case Study, Jun. 1997, American Psychologist, vol. 52, No. 6, pp. 630-634.

"Systematic Analysis and Scoring for Human Resources Candidate Recruitment", An IP.com Prior Art Database Technical Disclosure, Authors et. al.: Disclosed Anonymously, IP.com No. IPCOM000233528D, IP.com Electronic Publication: Dec. 11, 2013, pp. 1-4.

* cited by examiner

ROBUST SELECTION OF CANDIDATES

BACKGROUND OF THE INVENTION

The present invention relates generally to selecting candidates from a candidate pool, and also to identifying candidates that would benefit from interventional action.

In many areas of endeavor there is a fundamental need to select a subset of candidates from a larger candidate pool, or to select only those candidates that meet some predetermined criteria. This theme can be found in academic admissions, human resource talent management, sports team composition, consumer purchase decisions, supply chain management, financial instrument and product selection, business project and proposal evaluation, and government spending decisions, to name a few. For example, in the case of the conventional model used in academic admissions, heuristics are applied to performance data to identify high versus low performers, with low performers being rejected during a first cut. For applicants who make the cut, other characteristics are brought into consideration from supplemental capabilities data in a second round, and if a given student is still characterized as a high performer during this expanded assessment, then that given student is granted admission.

SUMMARY

According to an aspect of the present invention, there is a method, computer program product and/or system for evaluating candidates for selection that performs the following steps (not necessarily in the following order): (i) receives a first set of input parameters about a first aspect of candidates in a set of candidates; (ii) applies multiple scoring methods to the first set of input parameters to compute, for each scoring method, a score for the first aspect of each candidate; and (iii) selects a subset of zero or more candidates from the set of candidates by applying one or more selection criteria to the set of scores for the first aspect of each candidate. Each input parameter in the first set of input parameters is associated with zero or more values for each candidate.

DETAILED DESCRIPTION

Figure 1:
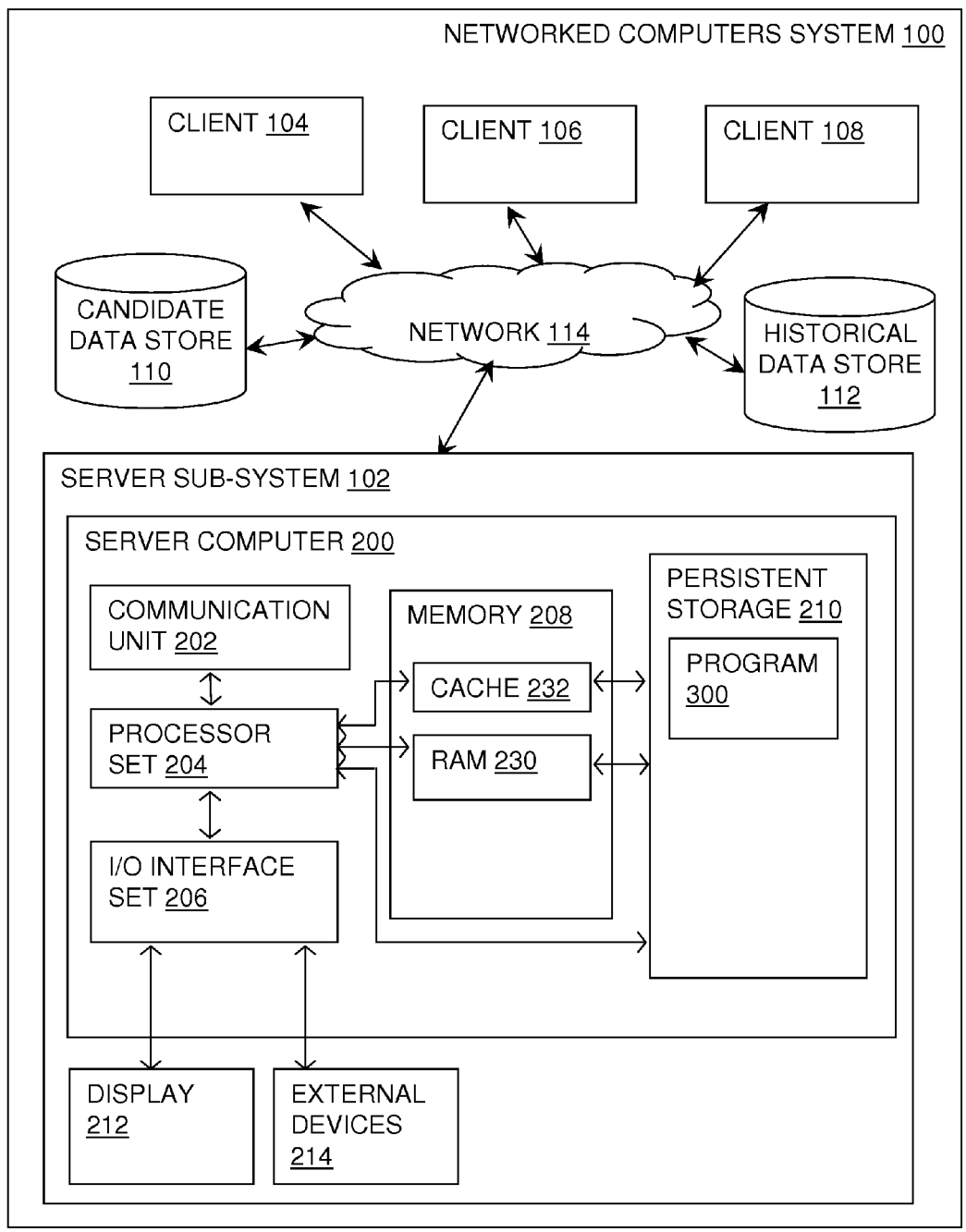
FIG. 1 is a block diagram view of a first embodiment of a system according to the present invention.

Some embodiments of the present invention evaluate an aspect of a candidate by applying multiple scoring methods to the same input data to generate multiple scores for that aspect. In some embodiments, scores are also computed for one or more other aspects of the candidate. Scores for each aspect considered are analyzed simultaneously to make a selection recommendation. In some embodiments, candidates recommended for selection are further reviewed in light of general historical data to determine if one or more intervention actions are likely to improve that candidate's future performance.

This Detailed Description section is divided into the following sub-sections: (i) The Hardware and Software Environment; (ii) Example Embodiment; (iii) Further Comments and/or Embodiments; and (iv) Definitions.

I. The Hardware and Software Environment

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

An embodiment of a possible hardware and software environment for software and/or methods according to the present invention will now be described in detail with reference to the Figures. FIG. 1 is a functional block diagram illustrating various portions of networked computers system 100, including: server sub-system 102; client sub-systems 104, 106, and 108; candidate data store 110; historical data store 112; communication network 114; server computer 200; communication unit 202; processor set 204; input/output (I/O) interface set 206; memory device 208; persistent storage device 210; display device 212; external device set 214; random access memory (RAM) devices 230; cache memory device 232; and program 300.

Sub-system 102 is, in many respects, representative of the various computer sub-system(s) in the present invention. Accordingly, several portions of sub-system 102 will now be discussed in the following paragraphs.

Sub-system 102 may be a laptop computer, tablet computer, netbook computer, personal computer (PC), a desktop computer, a personal digital assistant (PDA), a smart phone, or any programmable electronic device capable of communicating with the client sub-systems via network 114. Program 300 is a collection of machine readable instructions and/or data that is used to create, manage and control certain software functions that will be discussed in detail, below, in the Example Embodiment sub-section of this Detailed Description section.

Sub-system 102 is capable of communicating with other computer sub-systems via network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client sub-systems.

Sub-system 102 is shown as a block diagram with many double arrows. These double arrows (no separate reference numerals) represent a communications fabric, which provides communications between various components of sub-system 102. This communications fabric can be implemented with any architecture designed for passing data and/or control information between processors (such as microprocessors, communications and network processors, etc.), system memory, peripheral devices, and any other hardware components within a system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for sub-system 102; and/or (ii) devices external to sub-system 102 may be able to provide memory for sub-system 102.

Program 300 is stored in persistent storage 210 for access and/or execution by one or more of the respective computer processors 204, usually through one or more memories of memory 208. Persistent storage 210: (i) is at least more persistent than a signal in transit; (ii) stores the program (including its soft logic and/or data), on a tangible medium (such as magnetic or optical domains); and (iii) is substantially less persistent than permanent storage. Alternatively, data storage may be more persistent and/or permanent than the type of storage provided by persistent storage 210.

Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202, in these examples, provides for communications with other data processing systems or devices external to sub-system 102. In these examples, communications unit 202 includes one or more network interface cards. Communications unit 202 may provide communications through the use of either or both physical and wireless communications links. Any software modules discussed herein may be downloaded to a persistent storage device (such as persistent storage device 210) through a communications unit (such as communications unit 202).

I/O interface set 206 allows for input and output of data with other devices that may be connected locally in data communication with server computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. In these embodiments the relevant software may (or may not) be loaded, in whole or in part, onto persistent storage device 210 via I/O interface set 206. I/O interface set 206 also connects in data communication with display device 212.

Display device 212 provides a mechanism to display data to a user and may be, for example, a computer monitor or a smart phone display screen.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

II. Example Embodiment

For reasons of efficiency, consistency, neutrality, and so on, it may be of interest to automate at least some aspects of candidate selection. This automation is typically easiest for structured data, which is data that either has a pre-defined data model or is organized in a pre-defined manner. A numerical field in a relational database would be an example of this type of data. Unstructured data (for example, a paragraph of English natural language prose), or semi-structured data (like a free-form field), have traditionally been less amenable to automated processing than structured data, in part because of the considerable flexibility required to effectively process information in these forms. Data quality (for example, missing or invalid data) and data heterogeneity (such as continuous versus categorical attributes) can present additional challenges to rigid, automated processing techniques, particularly for data derived from unstructured or semi-structured sources.

Figure 2:
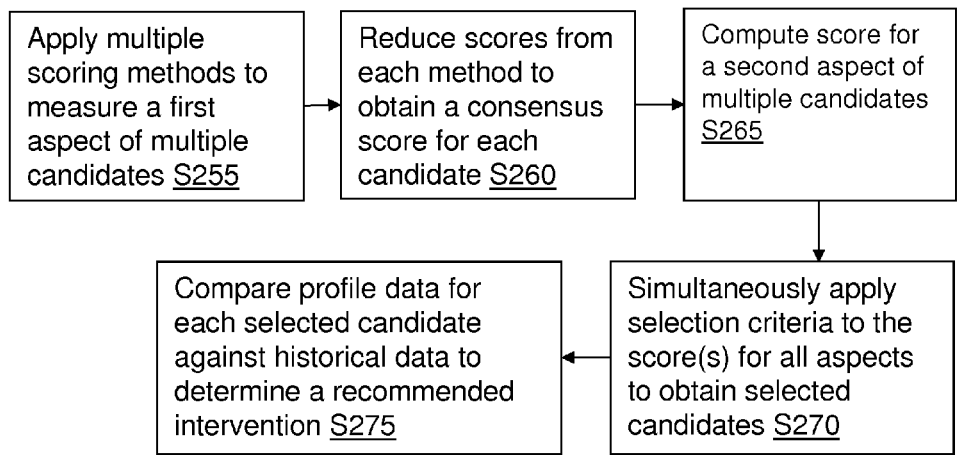
FIG. 2 is a flowchart showing a first embodiment method performed, at least in part, by the first embodiment system.
Figure 3:
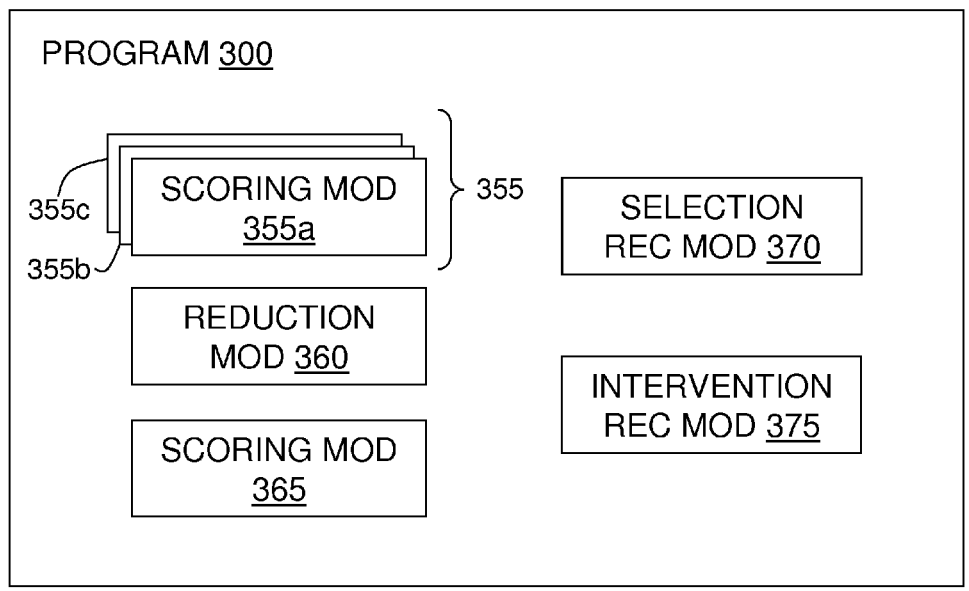
FIG. 3 is a block diagram view of a machine logic (for example, software) portion of the first embodiment system.

FIG. 2 shows flowchart 250 depicting a method for automated selection of candidates according to the present invention, capable of producing robust results even when faced with the difficulties described above. FIG. 3 shows program 300 for performing at least some of the method steps of flowchart 250. This method and associated software will now be discussed, over the course of the following paragraphs, with extensive reference to FIG. 2 (for the method step blocks) and FIG. 3 (for the software blocks).

Processing begins at step S255, where scoring modules ("mods") 355a, 355b, and 355c (collectively, scoring modules 355) each apply a different scoring method to data from candidate data store 110 (see FIG. 1) for a set of candidates. At step S255, three scores are computed for a single aspect (metric) of each candidate. More specifically, in this example: (i) the candidates are turtles of the same species that a pet store is considering buying; (ii) the first aspect of the candidate turtles is their leanness (the leaner the turtle is, the more suitable the turtle is for purchase by the pet store); and (iii) the three scoring methods are: (a) standard body mass index (BMI) (method applied by mod 355a), (b) Ponderal index (method applied by mod 355b), and (c) turtle head circumference (method applied by mod 355c). In this example, methods (a) and (b) use the exact same input data (that is, turtle mass and turtle length), but quantify turtle leanness in somewhat different ways using the same input data. On the other hand, method (c) uses completely different input data than the other two methods. Input data may include different attributes (parameters), such as mass, length, and head circumference, and/or multiple values for the same attribute, such as multiple measurements of these three attributes. However, each scoring method computes the same metric for (that is, a score for the same aspect of) each candidate.

Different scoring methods may: (i) handle missing or invalid data in different ways; (ii) convert heterogeneous data to a homogeneous format in different ways; and/or (iii) weigh, categorize, compare, and/or combine data points in different ways (see, for example, FIGS. 5A and 5B and accompanying discussion in subsection III, below). They may produce results that: (i) are directly comparable between methods, in the sense that if each method were completely accurate, each would arrive at the same exact result (for example, calculating body fat percentage via skinfold thickness, bioelectrical impedance analysis, and hydrostatic weighing); or (ii) are not directly comparable between methods, because they seek to characterize the aspect under analysis in different ways (say, for instance, by producing results in different units, such as with the standard BMI versus Ponderal calculations described above). The results may also be either: (i) interdependent, or correlated, whether theoretically or empirically, in the sense that knowing the value of the result of one method provides some information about the value of the result of another method (for example, knowing A=a+b=6, where x and y must be positive integers, also means that B=a*b must be 5 (=1*5), 8 (=2*4), or 9 (=3*3); or (ii) independent, even if the same data values are used for both calculations (for example, knowing the mean of 10 values gives no information about their variance).

In some embodiments of the present invention, the different scoring methods: (i) each take as input the same number of input parameters; (ii) each take as input only the same input parameters; and/or (iii) normalize all input parameters such that the results are comparable (that is, a value for normalized input parameter A is directly comparable with a value for normalized input parameter B). In general, any number of scoring methods may be used to score the aspect being analyzed. Moreover, the aspect may be defined broadly or narrowly. Percentage of body fat in the neck, general body leanness, general physical health, and overall health are examples of an increasingly broad aspect of candidate turtles.

Processing proceeds to step S260, where reduction mod 360 aggregates, combines, consolidates, eliminates, or otherwise reduces the scores from each method to arrive at a consensus score for the aspect of each candidate that was scored by multiple scoring mods 355. In this embodiment, aggregation is performed by: (i) normalizing the score from each of the three methods into a scalar from 0 to 100; and (ii) calculating an arithmetic average of the three normalized scores. Alternatively, other methods could be used, such as: (i) calculating a geometric average without normalization; (ii) averaging the nearest two out of three scores; (iii) normalizing and weighting the scores according to the relative perceived value of each scoring method and summing the results; or (iv) converting each score to a category rating and selecting the category into which the largest number of scores for that candidate fall. In some embodiments, if an acceptable level of consensus across the scoring methods is not reached, certain attributes from the input data set are removed and step S255 is then repeated with this trimmed data set until an acceptable level of consensus is reached (see, for example, steps S507 and S508 of FIG. 5A, discussed in subsection III below).

Aggregation step S260 is optional. For example, when the candidate evaluation also includes a score from a second aspect, an absolute selection rule such as the following might be used: "if three of the four scores from the first aspect are greater than X and the score from the second aspect is greater than Y, or if two of the four scores from the first aspect are greater than X and the composite score from the second aspect is greater than Y+C, then select that candidate).

Processing proceeds to step S265, where scoring mod 365 optionally produces a score for a different aspect of each candidate than the scores produced by scoring mods 355 using at least some different attributes than those used in step S255. Here, the pet store owner's embodiment considers a score for the degree of pyramiding of each turtle's shell as a second aspect of turtle market value. In general, scores for any number of aspects could be produced.

Processing proceeds to step S270, where selection recommendation mod 370 simultaneously applies selection criteria across all aspects with computed scores to determine which candidates should be selected. In the case at hand, selection recommendation mod 370 simultaneously evaluates: (i) a high/low score for leanness; and (ii) a high/low score for degree of pyramiding to determine which two of the three candidate turtles the shop owner should purchase. The 3 candidate turtles have scores as follows: (i) Turtle A: low body fat, low pyramiding; (ii) Turtle B: low body fat, high pyramiding; (iii) Turtle C: high body fat, low pyramiding. Selection criteria for selection recommendation mod 370 specify that turtles should be selected in the following order: (i) low body fat, low pyramiding turtles; then (ii) high body fat, low pyramiding turtles; then (iii) low body fat, high pyramiding turtles (the criteria further specify that high body fat, high pyramiding turtles should always be rejected). Therefore, selection recommendation mod 370 recommends selecting Turtle A (low body fat, low pyramiding) and Turtle C (high body fat, low pyramiding).

Processing proceeds to step S275, where intervention recommendation mod 375 optionally compares data about the candidates recommended for selection from candidate data store 110 (see FIG. 1) to historic data from historic data store 112 to determine what, if any, interventional steps should be taken for the selected candidates. The candidate data used in this step may or may not be the same data used in the selection process of the previous steps. The historic data used may include data comparable to the candidate data and/or information about interventions and subsequent outcomes. Continuing with the turtle example, intervention recommendation mod 375 compares the leanness and pyramiding data of Turtle A against historic data of actual and composite turtles similarly situated and finds no worthwhile intervention that would improve this turtle's market value. On the other hand, intervention recommendation mod 375 finds that putting Turtle C on a special diet for 6-8 weeks is likely to significantly improve Turtle C's market value (for example, by increasing leanness, leading to the more active and playful demeanor that consumers prefer). Intervention recommendation mod 375 therefore recommends this intervention for Turtle C.

III. Further Comments and/or Embodiments

Some embodiments of the present invention recognize the following facts, potential problems and/or potential areas for improvement with respect to the current state of the art: (i) current school/university admissions systems resort to sequential score-based segmentation, where the first round of elimination occurs by evaluating applicants on the basis of their standardized test scores, then the shortlisted applicants are put through a second round of evaluation wherein resumes, personal statements, and so on are manually read and given (subjective) scores; (ii) as a result, good candidates with slightly low test scores could be rejected, even though they may have excellent resumes, personal statements, or other competitive qualities; (iii) conventional approaches include: (a) sequential programmatic approaches, which can potentially miss good candidates, and (b) ad-hoc parallel approaches, which suffer from human bias; and/or (iv) there is currently an absence of a programmatic approach which combines capability and performance metrics to assist in academic program admissions decision making.

Additionally, some embodiments of the present invention recognize the following facts, potential problems and/or potential areas for improvement with respect to the current state of the art: (i) admission committees currently do not take preventive measures to predict who among the incoming class might have a lower than ideal performance toward the end of the first year; (ii) recommending remedial courses/programs could benefit such students and improve the graduation rate; (iii) to the extent they exist, conventional approaches to performance prediction include: (a) those based on performance metrics only, which can potentially miss some candidates that may benefit from interventional actions, and (b) ad-hoc approaches, which suffer from human bias; and/or (iv) for students that are admitted, there is no programmatic approach which combines capability and performance metrics to identify students who may benefit from being enrolled in a remedial program.

Accordingly, some embodiments of the present invention may include one, or more, of the following features, characteristics and/or advantages: (i) take as input a list of student capabilities defined by subject matter experts (SMEs); (ii) take as input students' standardized test scores; (iii) select students for admission based on a programmatic approach which combines capability and performance metrics by applying clustering and scoring techniques to perform the following tasks: (a) compute a robust capability score that combines a large number of capability metrics, (b) compute a performance score based on one or more performance metrics; and (c) combine the robust capability score with the performance score to obtain groupings of students; (iv) for students that are admitted, identify early the candidate students who could see improved performance from one or more proactive intervention actions, basing such identification on historical action, capability, and performance data; and/or (v) identify students to be enrolled in a remedial program based on a programmatic approach which combines capability and performance metrics.

Figure 4:
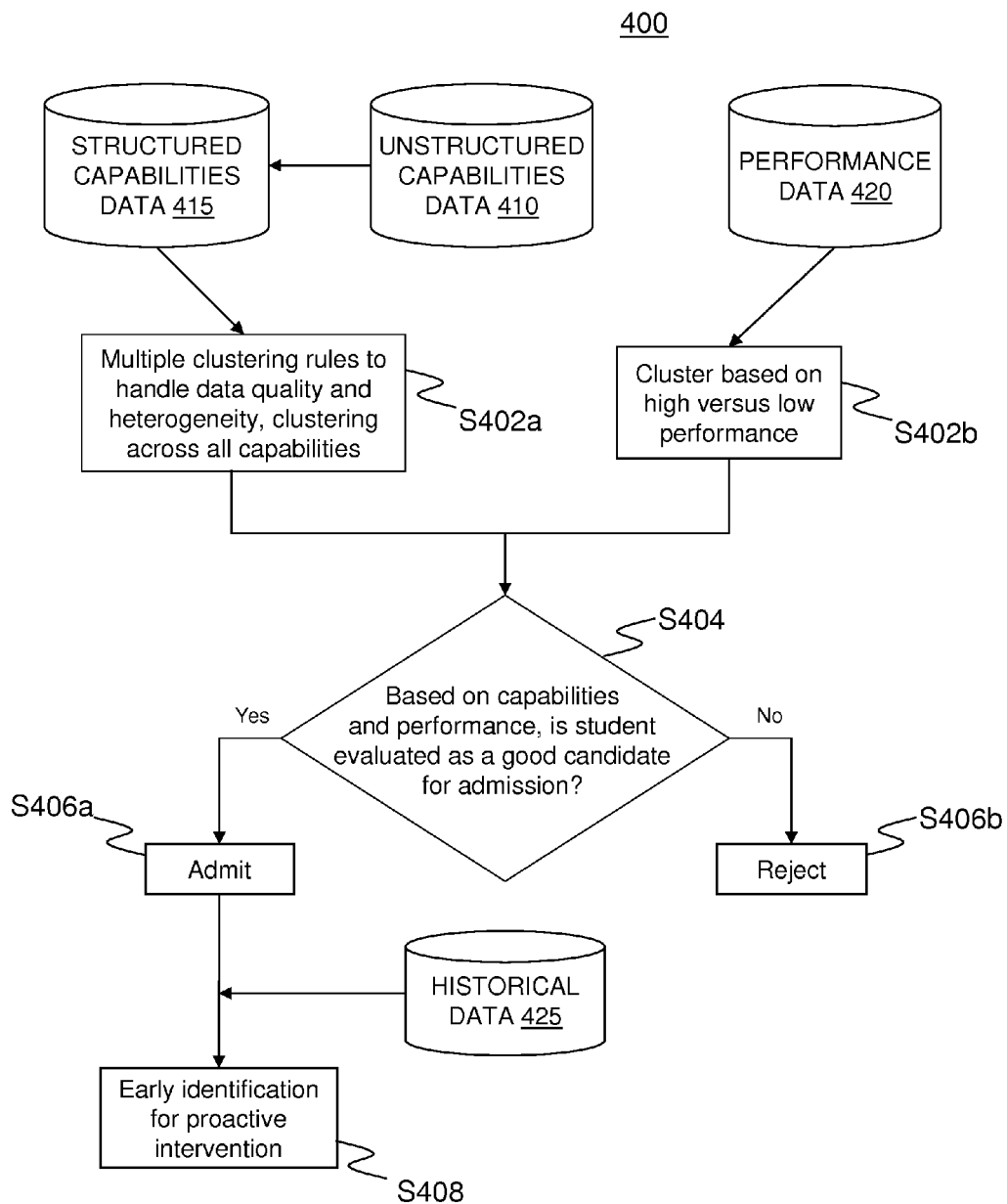
FIG. 4 is a first diagram view showing information that is helpful in understanding a second embodiment system according to the present invention.

Shown in FIG. 4 is diagram 400, illustrating a high-level view of a system incorporating these processes according to an embodiment of the present invention. FIG. 4 includes: unstructured capabilities data 410; structured capabilities data 415; performance data 420; historical data 425; and steps S402a, S402b, S404, S406a, S406b, and S408. SME-defined subjective and objective capabilities capture student-level metrics as capability or performance data. Performance data 420 includes data such as homework grades, standardized test scores, and advanced placement course results. Unstructured capabilities data 410 contains raw data from sources such as resumes, reference letters, and personal statements. The unstructured capabilities data is passed through data mining and text analytics software to produce structured capabilities data 415 based on student capability criteria and dimensions as defined at least in part by one or more SMEs. For example, structured capabilities data 415 might include such information as number of days absent, number of internships, number of sports played, and/or number and amount of scholarships. This structured data is combined and analyzed in step S402a by clustering across all SME-defined capabilities. Multiple clustering rules are used to provide robust results over a wide range of data quality and heterogeneity scenarios. (An example of structured capabilities data analysis is described below in connection with FIGS. 5A and 5B.) In parallel with this process, performance data 420 is used to cluster applicants into high and low performance categories in step S402b.

Results from both capability and performance assessments are then combined in step S404 to determine whether an applicant should be admitted (step S406a) or rejected (step S406b). An example of this part of the process is also detailed further below. In step S408, data for admitted students is compared with historical data 425 collected from other students whose data has been augmented by post-acceptance academic performance, effect of financial awards and/or coaching classes, and so on, to predict which newly admitted students might benefit from pro-active interventions that could help strengthen or maintain their academic performance going forward. For those admitted students who choose to enroll, this analysis can be repeated over the course of a student's tenure so that relevant opportunities may be presented to the student in a timely fashion.

Figure 5A:
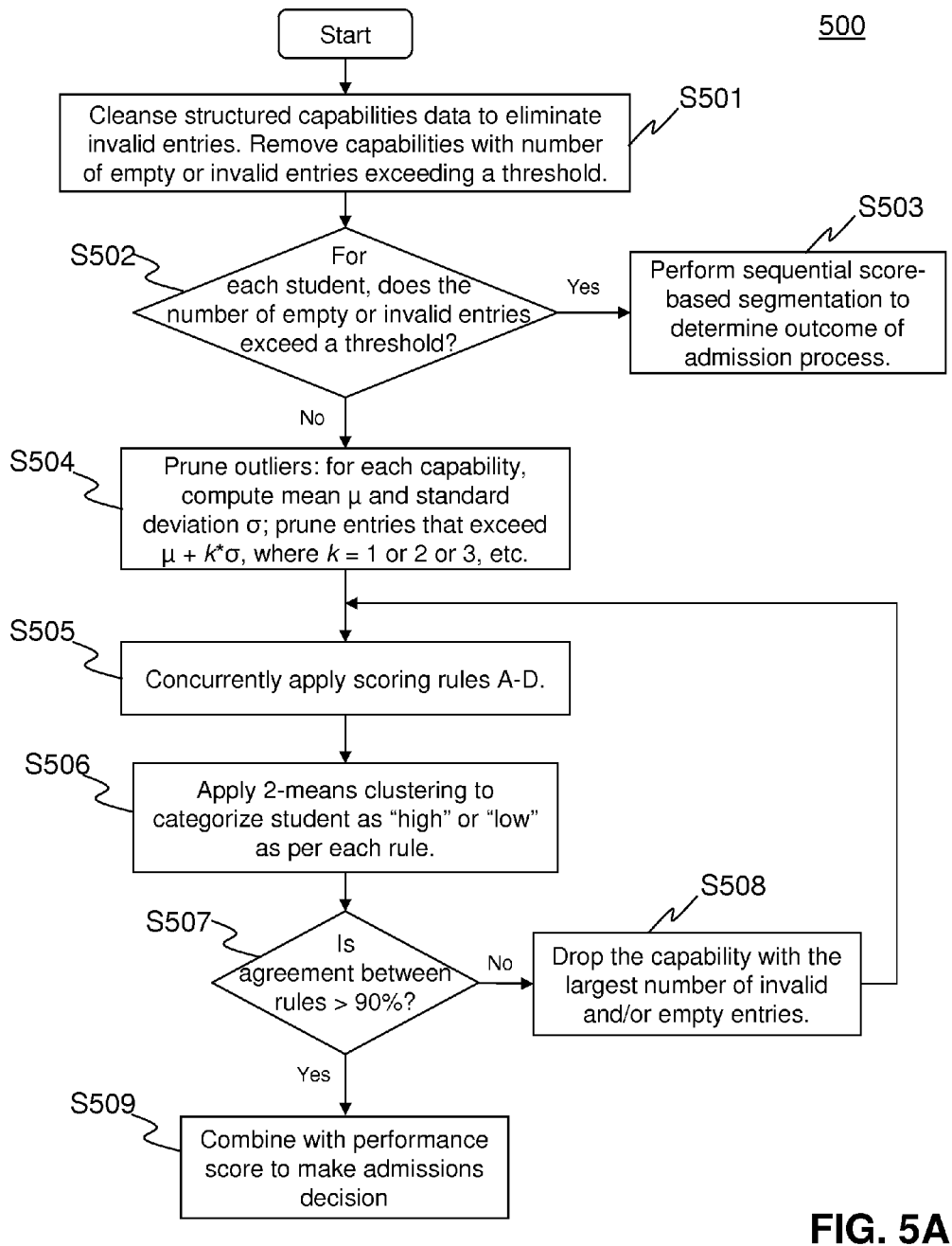
FIG. 5A is a first portion of a flowchart showing a second embodiment method preformed, at least in part, by the second embodiment system.
Figure 5B:
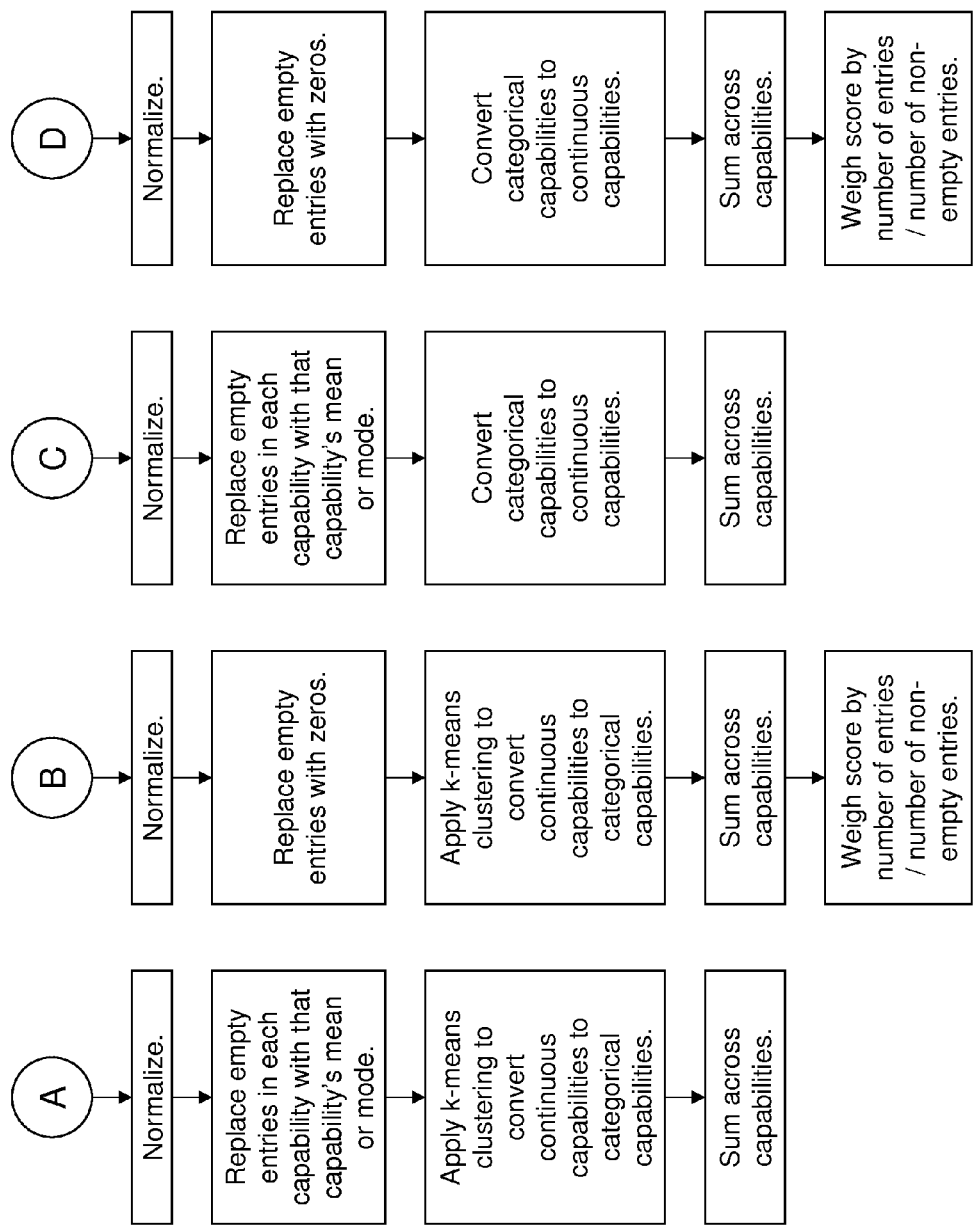
FIG. 5B is a second portion of a flowchart showing another portion of the second embodiment method.

FIGS. 5A and 5B present flowchart 500 detailing the process and rules used for analyzing structured capabilities data in some embodiments of the present invention (such as in step S402a of FIG. 4). This process produces robust results over a wide range of data quality and heterogeneity scenarios common with capabilities data. The process begins at step S501, where structured capabilities data is cleansed by removing capabilities for which the number of empty or invalid entries exceeds a threshold. For example, the threshold may be N/3, where N is the number of students in the applicant pool. If N/3+1 entries are empty or invalid for a particular capability, that capability is removed from consideration. Processing proceeds to step S502, where, for each student, if the number of empty or invalid entries exceeds a threshold, that student is removed from the simultaneous evaluation process (such as that presented in steps S402a, S402b, and S404 of FIG. 4) and is instead evaluated using a conventional, sequential score-based segmentation analysis (step S503) to determine the outcome of the admissions process. The threshold here may be, say, M/2, where M is the number of capabilities being analyzed. In step S504, a mean $\mu$ and a standard deviation $\sigma$ are then computed for each capability from the data of the students that remain, and using these parameters outliers are pruned. For example, for each capability, entries that exceed $\mu+k*\sigma$, where k is some value such as 1, 2, or 3, are pruned back to the limit value of $\mu+k*\sigma$.

Once these preliminary data cleansing and computational steps are complete, four capabilities scores are computed for each student in step S505 using scoring rules A through D. These scoring rules are presented in FIG. 5B. Each rule begins by normalizing the data. Empty entries in each capability are then replaced with that capability's mean or mode (rules A and C), or they are replaced with zeros (rules B and D). K-means clustering is applied to the resulting data, with continuous capabilities being converted to categorical capabilities (rules A and B), or categorical capabilities are converted to continuous capabilities without k-means clustering (rules C and D). In this way, heterogeneous data are transformed into a combinable, homogeneous format. For each student, the results are then summed across capabilities to compute a capability score, with that score adjusted in rules B and D by multiplying by the total number of entries divided by the number of non-empty entries for that student. For each of the four resulting scores, 2-means clustering is applied in step S506 (FIG. 5A) to categorize each student as "high" or "low" for the capabilities assessment according to that rule. If the four rules agree across more than a certain percentage of the applicant pool—here, 90%—on which category each student falls into (step S507), the capabilities results are combined with the performance results (step S509) to make an admissions decision (see also S404 in FIG. 4). Alternatively, if the four rules do not yield more than a threshold degree of consistency across the applicant pool, the capability with the largest number of invalid and/or empty entries is dropped in step S508, and the analysis is repeated from the four rules stage of step S505 until consistent results are obtained.

As exemplified in the Figures discussed above, some embodiments of the present invention may include one, or more, of the following features, characteristics and/or advantages: (i) apply uni-dimensional clustering-based rules for capability assessment to handle limitations associated with data size, heterogeneity, quality, and reliability; (ii) include four heuristic rules to score students and classify them into two categories: (a) above the line, or (b) below the line, based on applying different options for (a) combining continuous and categorical data, and/or (b) handling missing data elements; and/or (iii) combine the use of multiple scoring models to drive robust results.

Given a sample data set, application of the four clustering-based rules for capability assessment presented in FIGS. 5A and 5B can produce greater than 90% pair-wise agreement in some embodiments of the present invention, as shown in Table 1 below. For example, Rule A and Rule B agree in 95.4% of instances on which students they classify as above or below the line—they disagree on 12 students out of 260, or 4.6% of the population. The models agree on classification in over 90% of the instances. The results are robust to capability assessment scoring rules.

TABLE 1

Capability assessment scoring rules agreement matrix

|         | Rule A  | Rule B  | Rule C  | Rule D |
| ------- | ------- | ------- | ------- | ------ |
| Rule A  | 100%    | —       | —       | —      |
| Rule B  | 95.38%  | 100%    | —       | —      |
| Rule C  | 95.00%  | 94.23%  | 100%    | —      |
| Rule D  | 93.08%  | 95.38%  | 96.54%  | 100%   |

In some embodiments of the present invention, students are classified into "admit," "don't admit," and "admit with increased supervision" categories. For example, suppose 173 students have valid standardized test performance data, of which 106 students are classified as below the line by one or more of the scoring rules and 67 students are classified as above the line by one or more of the scoring rules. In this example, students are classified as "don't admit" if (i) they are below the line capability assessment; and (ii) standardized test performance is 75% attainment or lower (where "75% attainment" corresponds to half standard deviation less than mean standardized test performance). This scenario is laid out in Table 2.

TABLE 2

Standardized test performance by capabilities assessment category

| Classification category | Number of students | Mean test performance | Median test performance | Percentage of students with high test performance |
| --- | --- | --- | --- | --- |
| Above the line | 67 (=41 + 26) | 123% | 109% | 61% |
| Below the line | 106 (=33 + 73) | 115% | 94% | 69% |

Out of the 173 students, 33 are identified as low on both the capability assessment and standardized test performance and are therefore classified as "don't admit." In addition, 41 are identified as above the line on the capability assessment and have a higher performance and are therefore classified as "admit." This leaves 99 students that may benefit from training under additional supervision during the first year. Overall, there is some evidence to indicate capabilities are reflective of standardized test performance in this example.

Figure 6:
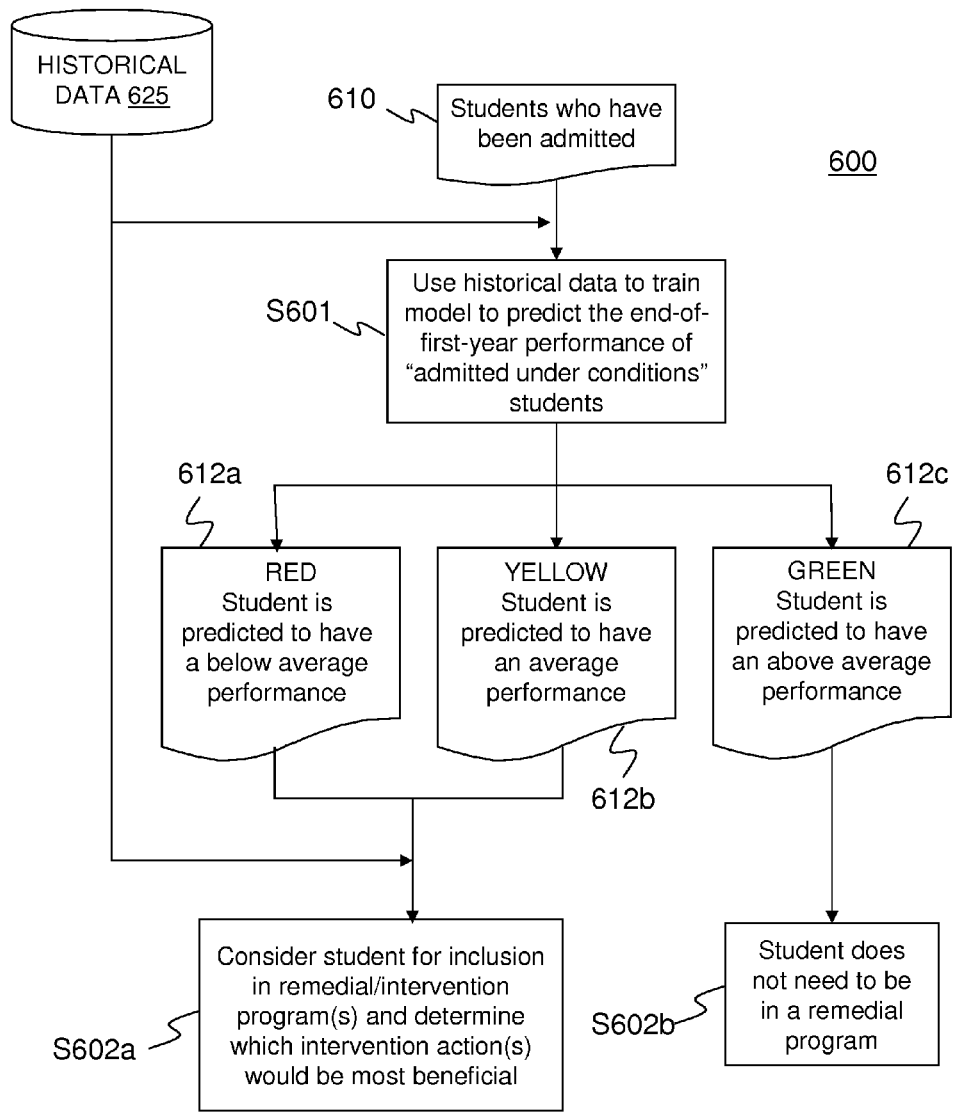
FIG. 6 is a second diagram view showing information that is helpful in understanding the second embodiment system.

Shown in FIG. 6 is diagram 600, an example illustration of how historical data can be applied to predict the performance of admitted students and identify candidates early who might benefit from proactive intervention. This process corresponds to step S408 in FIG. 4. In this example, historical data 625 is used to train a model to predict the end-of-first-year performance of admitted students, particularly those who have been "admitted under conditions." Historical data 625 includes both initial capabilities and performance data of students admitted during previous admissions cycles as well as their subsequently acquired characteristics (such as financial aid awards or coaching classes) and performance. In step S601, when this model is then fed with data about currently admitted students 610, it predicts which students are likely to have a below-average performance (red group, 612a), an average performance (yellow group, 612b), or an above-average performance (green group, 612c). Students in the former two groups are considered for inclusion in remedial/interventional programs in step S602a, with historical data 625 and predictive analysis again used to help determine what interventions might be beneficial and to quantify their expected benefits on a student-by-student basis. Students who are predicted to be above-average performers are not considered for inclusion in remedial/interventional programs (step S602b), but, along with their peers from the other two groups, may nevertheless be reevaluated again as new information is obtained over the course of their studies.

Figure 7:
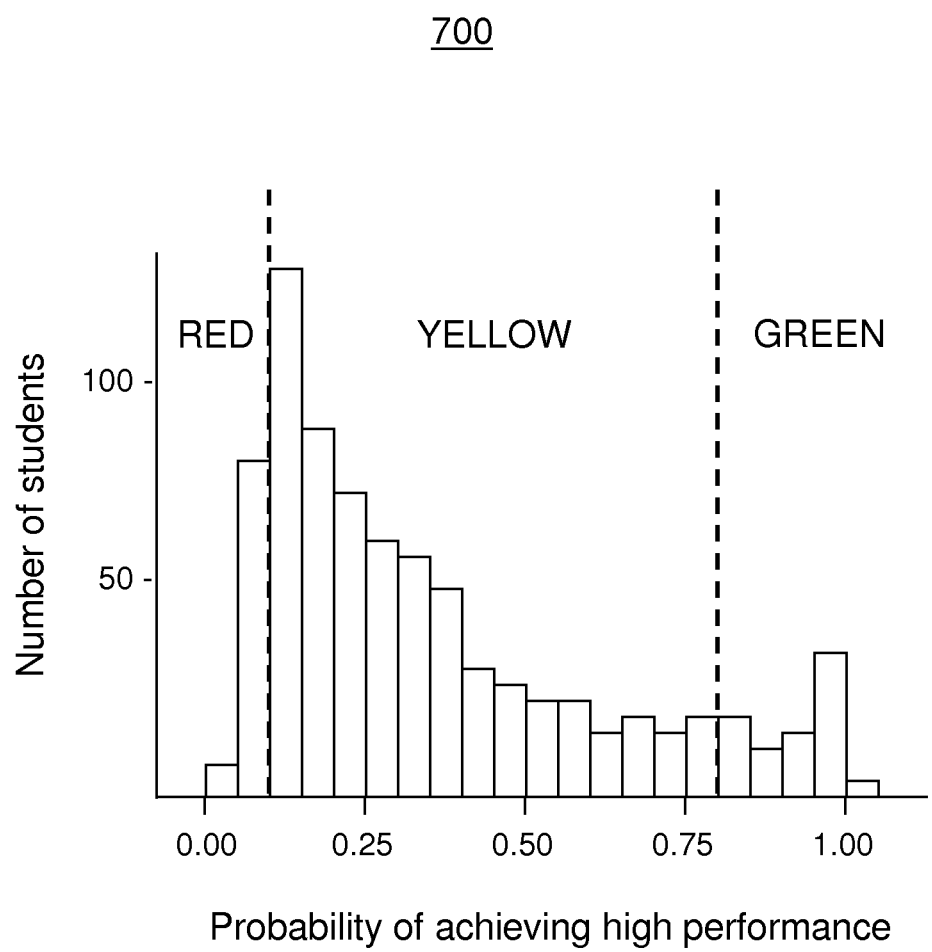
FIG. 7 is a graph showing information that is helpful in understanding the second embodiment system.

Shown in FIG. 7 is chart 700, illustrating predicted outcome of student performance used to categorize student performance risk level. Chart 700 is developed from models based on historical capability and performance data which are then used to predict the likelihood that students will have high performance, for example in their freshman year. The population of students is partitioned into groups where actions are likely to be most effective (that is, where there is a high expected return on investment (ROI)) using predictive model output. Here, the population is divided into three risk groups from highest risk to lowest risk: Red, Yellow, and Green, indicating the risk of failing to achieve a performance target. Actions can then be tailored based on predicted risk level to maximize ROI. For example, students classified in the Yellow group may be offered the opportunity to participate in any one of several special programs, while students classified in the Red group may be placed in a particular special program as a condition of enrollment.

Some embodiments of the present invention may include one, or more, of the following features, characteristics and/or advantages: (i) identify students for admission and/or for performance improvement remedial program(s) to maximize return on investment; (ii) include programmatic methods to admit students non-sequentially; (iii) use data sources that permit evaluation of candidates in terms of performance (for example, standardized test scores) and/or capabilities (for example, number of foreign languages known); (iv) evaluate candidates in terms of performance and/or capabilities; (v) simultaneously evaluate along two or more dimensions to identify desirable candidates (for instance, rather than shortlisting candidates on the basis of one dimension before considering other dimension(s)); (vi) evaluate performance and capabilities simultaneously using a statistical analysis procedure; (vii) score candidates along two dimensions (such as performance and capabilities) simultaneously; (viii) consider a combination of subjective and objective metrics for capabilities (examples of subjective metrics include perceived intensity of a high school AP course, perceived school quality, and quality of statement of purpose, essays, and the like, while examples of object metrics include number of days absent and number of officer positions held); (ix) use clustering techniques to classify candidates as being 'high' or 'low' along each of two or more dimensions; (x) accept candidates who are classified as 'high' on both (all) dimensions; and/or (xi) score candidates simultaneously in two or more dimensions by classifying candidates (such as 'high' versus 'low') along each dimension to identify those who have high scores in both (all) dimensions.

Alternatively or in addition, some embodiments of the present invention may include one, or more, of the following features, characteristics and/or advantages: (i) identify candidates with high capability but low performance so that corrective actions can be taken; (ii) include programmatic methods to identify and/or select students for remedial programs; (iii) use performance of previously accepted candidates to recommend/apply remedial actions to newly accepted candidates; (iv) consider multiple dimensions simultaneously while handling data quality issues; (v) use scoring methods that effectively handle data reliability and heterogeneity issues; (vi) use multiple scoring methods to handle data heterogeneity; (vii) check agreement in the candidates' scores as per each of the multiple methods to identify capabilities that skew scores due to a large number of empty or invalid entries; and/or (viii) leverage clustering techniques as well as multiple scoring methods to avoid choosing weightings (for example, subject matter experts may score essays on a scale of 1-10, features may be pruned and normalized prior to statistical analyses, and four clustering rules may then be used to compute different scores, all without applying weights to capabilities with respect to each other) and/or to ensure reliability in the presence of data quality issues.

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein that are believed as maybe being new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

Capabilities/performance: capabilities represent skills, talent, experience, and/or other factors, including environmental factors, of an entity, such as an individual; performance is the result, or outcome, of the application of skills, talent, experience, and/or other factors.

Parameter: a data field that may or may not contain a value for a given candidate; sport type, high school grade point average, and net asset value are all examples of parameters.

What is claimed is:

1. A method for evaluating candidates for selection, the method comprising:
   receiving a first set of input parameters about a first aspect of the candidates in a set of candidates;
   applying multiple scoring methods to the first set of input parameters to compute, for each scoring method, a score for the first aspect of each candidate;
   evaluating an agreement between or among the multiple scoring methods by comparing the computed scores of the multiple scoring methods;
   responsive to the evaluated agreement not meeting or exceeding a threshold level, (i) updating the first set of input parameters by dropping one or more parameters from the first set of input parameters, and (ii) repeating application of the multiple scoring methods with the updated first set of input parameters until the agreement meets the threshold level; and
   selecting a subset of one or more candidates from the set of candidates by applying one or more selection criteria to a set of the computed scores corresponding to the agreement meeting the threshold for the first aspect of each candidate;
   wherein:
   each input parameter in the first set of input parameters is associated with zero or more values for each candidate; and
   at least the application of one or more of the multiple scoring methods is performed by computer software running on computer hardware.

2. The method of claim 1, wherein each scoring method of the multiple scoring methods:
   takes as input a same number of input parameters from the first set of input parameters as each other scoring method of the multiple scoring methods; and
   takes as input same input parameters from the first set of input parameters as each other scoring method of the multiple scoring methods.

3. The method of claim 1, further comprising:
   computing a score for a second aspect of each candidate using a second set of input parameters;
   wherein:
   each input parameter in the second set of input parameters is associated with zero or more values for each candidate;
   at least one input parameter in either the first set of input parameters or the second set of input parameters is not common to both sets of input parameters; and
   the selection of the subset of candidates includes simultaneous evaluation of at least one first aspect score and one second aspect score.

4. The method of claim 3, wherein the first aspect is candidate capabilities and the second aspect is candidate performance.

5. The method of claim 1, further comprising:
identifying a selected candidate whose performance could benefit from one or more intervention actions by comparing characteristics of the selected candidate to historic characteristics and performance data about other candidates or other individuals, groups, or entities similarly situated with respect to the compared characteristics; and
recommending the selected candidate for the one or more intervention actions.

6. The method of claim 1, wherein a first scoring method of the multiple scoring methods includes normalizing each input parameter in the first set of input parameters such that values of the normalized input parameters are comparable.

7. The method of claim 1, wherein a first scoring method of the multiple scoring methods includes dealing with missing or invalid data in a different way than a second scoring method of the multiple scoring methods.

8. The method of claim 1, wherein a first scoring method of the multiple scoring methods converts heterogeneous data formats to a homogeneous data format in a different way than a second scoring method of the multiple scoring methods.

9. The method of claim 1, wherein the candidates are student admissions candidates.

10. A computer program product comprising:
a non-transitory machine readable storage device; and
computer code stored on the non-transitory machine readable storage device, with the computer code including instructions for causing a set of one or more hardware processors to perform operations including the following:
receiving a first set of input parameters about a first aspect of the candidates in a set of candidates;
applying multiple scoring methods to the first set of input parameters to compute, for each scoring method, a score for the first aspect of each candidate;
evaluating an agreement between or among the multiple scoring methods by comparing the computed scores of the multiple scoring methods;
responsive to the evaluated agreement not meeting or exceeding a threshold level, (i) updating the first set of input parameters by dropping one or more parameters from the first set of input parameters, and (ii) repeating application of the multiple scoring methods with the updated first set of input parameters until the agreement meets the threshold level; and
selecting a subset of one or more candidates from the set of candidates by applying one or more selection criteria to a set of the computed scores corresponding to the agreement meeting the threshold for the first aspect of each candidate;
wherein:
each input parameter in the first set of input parameters is associated with zero or more values for each candidate.

11. The product of claim 10, wherein each scoring method of the multiple scoring methods:
takes as input a same number of input parameters from the first set of input parameters as each other scoring method of the multiple scoring methods; and
takes as input same input parameters from the first set of input parameters as each other scoring method of the multiple scoring methods.

12. The product of claim 10, further comprising:
computing a score for a second aspect of each candidate using a second set of input parameters;
wherein:
each input parameter in the second set of input parameters is associated with zero or more values for each candidate;
at least one input parameter in either the first set of input parameters or the second set of input parameters is not common to both sets of input parameters; and
the selection of the subset of candidates includes simultaneous evaluation of at least one first aspect score and one second aspect score.

13. The product of claim 10, further comprising:
identifying a selected candidate whose performance could benefit from one or more intervention actions by comparing characteristics of the selected candidate to historic characteristics and performance data about other candidates or other individuals, groups, or entities similarly situated with respect to the compared characteristics; and
recommending the selected candidate for the one or more intervention actions.

14. The product of claim 10, wherein a first scoring method of the multiple scoring methods includes normalizing each input parameter in the first set of input parameters such that values of the normalized input parameters are comparable.

15. A computer system for evaluating candidates for selection, the computer system comprising:
a set of one or more hardware processors; and
a computer readable storage medium;
wherein:
computer code, stored on the computer readable storage medium, including instructions for causing the set of one or more hardware processors to perform operations including the following:
receiving a first set of input parameters about a first aspect of the candidates in a set of candidates;
applying multiple scoring methods to the first set of input parameters to compute, for each scoring method, a score for the first aspect of each candidate;
evaluating an agreement between or among the multiple scoring methods by comparing the computed scores of the multiple scoring methods;
responsive to the evaluated agreement not meeting or exceeding a threshold level, (i) updating the first set of input parameters by dropping one or more parameters from the first set of input parameters, and (ii) repeating application of the multiple scoring methods with the updated first set of input parameters until the agreement meets the threshold level; and
selecting a subset of one or more candidates from the set of candidates by applying one or more selection criteria to a set of the computed scores corresponding to the agreement meeting the threshold for the first aspect of each candidate;
wherein:
each input parameter in the first set of input parameters is associated with zero or more values for each candidate.

16. The system of claim 15, wherein each scoring method of the multiple scoring methods:
takes as input a same number of input parameters from the first set of input parameters as each other scoring method of the multiple scoring methods; and
takes as input same input parameters from the first set of input parameters as each other scoring method of the multiple scoring methods.

17. The system of claim 15, wherein the operations further include:
  computing a score for a second aspect of each candidate using a second set of input parameters; and
  wherein:
    each input parameter in the second set of input parameters is associated with zero or more values for each candidate;
    at least one input parameter in either the first set of input parameters or the second set of input parameters is not common to both sets of input parameters; and
    the selection of the subset of candidates includes simultaneous evaluation of at least one first aspect score and one second aspect score.

18. The system of claim 15, wherein the operations further include:
  identifying a selected candidate whose performance could benefit from one or more intervention actions by comparing characteristics of the selected candidate to historic characteristics and performance data about other candidates or other individuals, groups, or entities similarly situated with respect to the compared characteristics; and
  recommending the selected candidate for the one or more intervention actions.

19. The system of claim 15, wherein a first scoring method of the multiple scoring methods includes normalizing each input parameter in the first set of input parameters such that values of the normalized input parameters are comparable.

20. The system of claim 15, wherein a first scoring method of the multiple scoring methods converts heterogeneous data formats to a homogeneous data format in a different way than a second scoring method of the multiple scoring methods.

* * * * *